US012426909B2

United States Patent
Cowley

(10) Patent No.: US 12,426,909 B2
(45) Date of Patent: Sep. 30, 2025

(54) ULTRASONIC TRANSDUCER ASSEMBLY AND ULTRASONIC SURGICAL INSTRUMENT INCORPORATING THE SAME

(71) Applicant: Covidien LP, Mansfield, MA (US)

(72) Inventor: Matthew S. Cowley, Frederick, CO (US)

(73) Assignee: Covidien LP, Mansfield, MA (US)

( * ) Notice: Subject to any disclaimer, the term of this patent is extended or adjusted under 35 U.S.C. 154(b) by 961 days.

(21) Appl. No.: 17/618,787

(22) PCT Filed: Jun. 10, 2020

(86) PCT No.: PCT/US2020/036939
§ 371 (c)(1),
(2) Date: Dec. 13, 2021

(87) PCT Pub. No.: WO2021/006984
PCT Pub. Date: Jan. 14, 2021

(65) Prior Publication Data
US 2022/0240970 A1   Aug. 4, 2022

Related U.S. Application Data

(60) Provisional application No. 62/871,293, filed on Jul. 8, 2019.

(51) Int. Cl.
*B06B 1/06* (2006.01)
*A61B 17/32* (2006.01)

(52) U.S. Cl.
CPC .... *A61B 17/320068* (2013.01); *B06B 1/0611* (2013.01); *A61B 2017/320082* (2017.08); *B06B 2201/76* (2013.01)

(58) Field of Classification Search
CPC .. B06B 1/0611; B06B 1/06; A61B 17/320068
(Continued)

(56) References Cited

U.S. PATENT DOCUMENTS 6,063,050 A   5/2000  Manna et al.
6,786,383 B2  9/2004  Stegelmann
(Continued)

FOREIGN PATENT DOCUMENTS

EP    2338426 A1   6/2011
WO    2018098201 A1  5/2018

OTHER PUBLICATIONS

International Search Report and Written Opinion issued in corresponding International Application No. PCT/US2020/036939 dated mailed Sep. 22, 2020, 9 pages.
(Continued)

*Primary Examiner* — Derek J Rosenau

(57) ABSTRACT

An ultrasonic transducer assembly of an ultrasonic surgical instrument includes a piezoelectric stack, an ultrasonic horn secured to and extending distally from the piezoelectric stack, and a casing. The ultrasonic horn includes a body and a nose extending distally from the body. The casing is disposed about the piezoelectric stack and the body of the ultrasonic horn. The casing defines a distal opening through which the nose of the ultrasonic horn extends. The casing is hermetically sealed to the ultrasonic horn about the distal opening to define a hermetically sealed interior enclosing the piezoelectric stack and the body of the ultrasonic horn therein.

20 Claims, 5 Drawing Sheets

(58) Field of Classification Search
USPC .................................................. 310/322, 334
See application file for complete search history.

(56) References Cited

U.S. PATENT DOCUMENTS

| | | |
|---|---|---|
| 8,372,101 B2 | 2/2013 | Smith et al. |
| 8,531,064 B2 | 9/2013 | Robertson et al. |
| 8,951,272 B2 | 2/2015 | Robertson et al. |
| 9,326,812 B2 | 5/2016 | Waaler et al. |
| 10,245,064 B2 | 4/2019 | Rhee et al. |
| 2004/0006269 A1 | 1/2004 | Novak et al. |
| 2010/0106173 A1 | 4/2010 | Yoshimine |
| 2012/0261066 A1 | 10/2012 | Smith et al. |
| 2015/0157354 A1 | 6/2015 | Bales, Jr. et al. |
| 2016/0121143 A1 | 5/2016 | Mumaw et al. |
| 2016/0206900 A1 | 7/2016 | Haberstich et al. |
| 2017/0319229 A1 | 11/2017 | Brown et al. |
| 2018/0014846 A1* | 1/2018 | Rhee .............. A61B 17/320092 |
| 2018/0014848 A1 | 1/2018 | Messerly et al. |
| 2020/0107852 A1 | 4/2020 | Lee et al. |

OTHER PUBLICATIONS

Extended European Search Report issued in corresponding European Application No. 20836697.1 dated May 16, 2023, 6 pages.
EP Examination Report for EP Application No. 20 836 697.1 mailed Jun. 28, 2024.

* cited by examiner

ULTRASONIC TRANSDUCER ASSEMBLY AND ULTRASONIC SURGICAL INSTRUMENT INCORPORATING THE SAME

CROSS-REFERENCE TO RELATED APPLICATIONS

This application is a U.S. National Stage Application filed under 35 U.S.C. § 371 (a) of International Patent Application No. PCT/US2020/036939, filed Jun. 10, 2020, which claims the benefit of, and priority to, U.S. Provisional Patent Application No. 62/871,293 filed Jul. 8, 2019, the entire contents of each of which is hereby incorporated herein by reference.

BACKGROUND

Technical Field

The present disclosure relates to ultrasonic surgical instruments and, more particularly, to an ultrasonic transducer assembly and ultrasonic surgical instrument including the same.

Background of Related Art

Ultrasonic surgical instruments utilize ultrasonic energy, i.e., ultrasonic vibrations, to treat tissue. More specifically, ultrasonic surgical instruments utilize mechanical vibration energy transmitted at ultrasonic frequencies to coagulate, cauterize, fuse, seal, cut, desiccate, and/or fulgurate tissue to effect hemostasis.

Ultrasonic surgical instruments typically employ a transducer coupled to a handle of the ultrasonic surgical instrument and configured to produce ultrasonic energy for transmission along a waveguide to an end effector of the ultrasonic surgical instrument that is designed to treat tissue with the ultrasonic energy. The transducer may be driven by an ultrasonic generator that is on-board, e.g., on or within the handle of the ultrasonic surgical instrument, or remotely disposed, e.g., as a set-top box connected to the ultrasonic surgical instrument via a surgical cable. The end effector of the ultrasonic surgical instrument may include a blade that receives the ultrasonic energy from the waveguide for application to tissue and a jaw member configured to clamp tissue between the blade and the jaw member to facilitate treatment thereof.

SUMMARY

As used herein, the term "distal" refers to the portion that is described which is further from a user, while the term "proximal" refers to the portion that is being described which is closer to a user. Further, any or all of the aspects described herein, to the extent consistent, may be used in conjunction with any or all of the other aspects described herein.

Provided in accordance with aspects of the present disclosure is an ultrasonic transducer assembly of an ultrasonic surgical instrument. The ultrasonic transducer assembly includes a piezoelectric stack, an ultrasonic horn, and a casing. The ultrasonic horn is secured to and extends distally from the piezoelectric stack. The ultrasonic horn includes a body and a nose extending distally from the body. The casing is disposed about the piezoelectric stack and the body of the ultrasonic horn. The casing defines a distal opening through which the nose of the ultrasonic horn extends and is hermetically sealed to the ultrasonic horn about the distal opening to define a hermetically sealed interior enclosing the piezoelectric stack and the body of the ultrasonic horn therein.

In an aspect of the present disclosure, the casing is welded to the ultrasonic horn along a weld joint surrounding the distal opening. In such aspects, the ultrasonic horn may include a flange disposed between the body and the nose. The flange is disposed within the hermetically sealed interior adjacent the distal opening and overlapping the weld joint.

In another aspect of the present disclosure, the casing is hermetically sealed to the ultrasonic horn at a nodal point along the ultrasonic horn.

In still another aspect of the present disclosure, the casing includes at least two casing components hermetically sealed to one another. In such aspects, the at least two casing components may be welded to one another along at least one additional weld joint. Further, one of the at least two casing components may include a flange disposed within the hermetically sealed interior and overlapping the at least one additional weld joint.

In yet another aspect of the present disclosure, a contact assembly is hermetically sealed within one or more windows defined through the casing. The contact assembly includes a plurality of contacts extending from the hermetically sealed interior to an exterior of the casing. In such aspects, the contact assembly may further include a frame electrically isolating the plurality of contacts from the casing.

In still yet another aspect of the present disclosure, at least one of the contacts of the contact assembly is configured to communicate a drive signal into the hermetically sealed interior and/or at least another one of the contacts is configured to communicate a data signal from the hermetically sealed interior.

An ultrasonic surgical instrument provided in accordance with aspects of the present disclosure includes a handle assembly and an elongated assembly. The handle assembly includes a housing and an ultrasonic transducer assembly according to any of the aspects detailed above or otherwise herein. The elongated assembly extends distally from the handle assembly. The elongated assembly includes a waveguide that is configured to engage the nose of the ultrasonic horn and that defines a blade at a distal end thereof. Ultrasonic energy produced by the piezoelectric stack is transmitted along the ultrasonic horn and the waveguide to the blade for treating tissue adjacent the blade.

In an aspect of the present disclosure, a contact assembly is hermetically sealed within one or more windows defined through the casing. The contact assembly includes a plurality of slip contacts extending from the hermetically sealed interior to an exterior of the casing. In such aspects, each of a plurality of ring contacts disposed within the handle assembly may be configured to slidable couple to a corresponding slip contact of the plurality of slip contacts. At least one pair of a ring contact and a corresponding slip contact may be configured to communicate a drive signal into the hermetically sealed interior. Additionally or alternatively, at least one pair of a ring contact and a corresponding slip contact may be configured to communicate a data signal from the hermetically sealed interior.

BRIEF DESCRIPTION OF THE DRAWINGS

The above and other aspects and features of the present disclosure will become more apparent in light of the following detailed description when taken in conjunction with the accompanying drawings wherein like reference numerals identify similar or identical elements.

DETAILED DESCRIPTION

Figure 1:
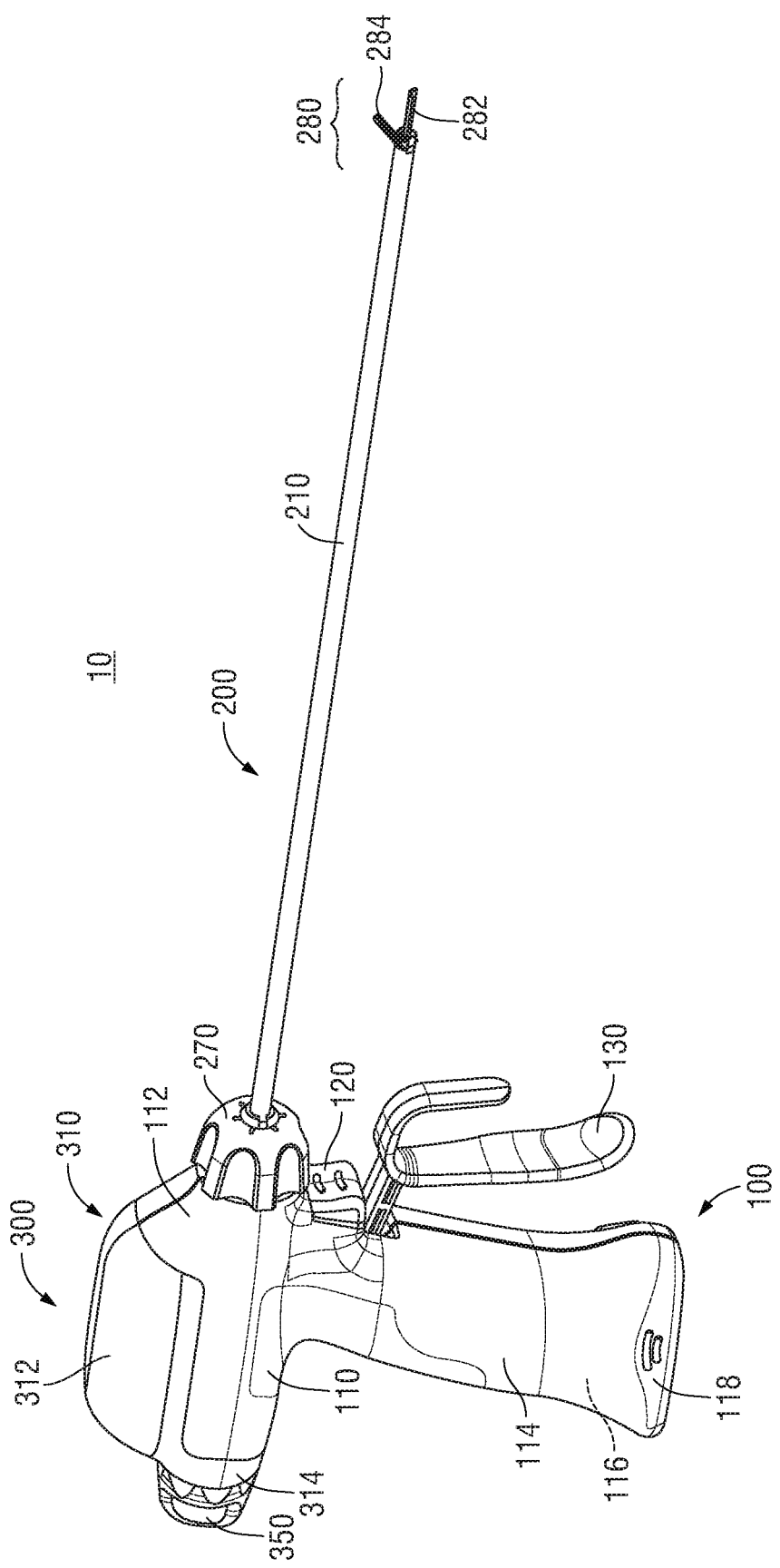
FIG. 1 is a side, perspective view of an ultrasonic surgical instrument provided in accordance with the present disclosure.
Figure 2:
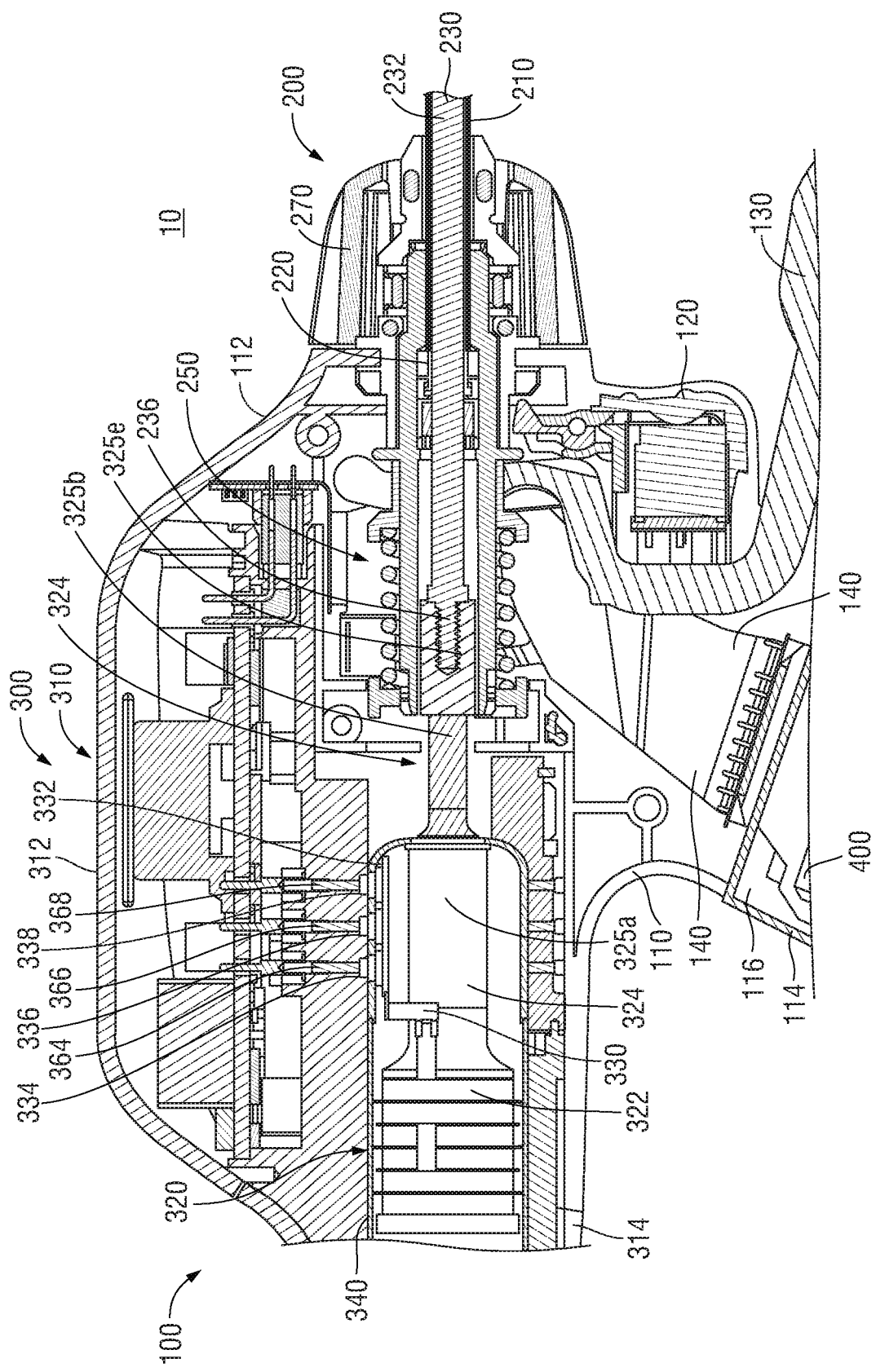
FIG. 2 is an enlarged, side, longitudinal, cross-sectional view of a proximal portion of the ultrasonic surgical instrument of FIG. 1.

Referring to FIGS. 1 and 2, an ultrasonic surgical instrument provided in accordance with the present disclosure is shown generally identified by reference numeral 10. Ultrasonic surgical instrument 10 includes a handle assembly 100 and an elongated assembly 200 extending distally from handle assembly 100. Handle assembly 100 includes a housing 110 defining a body portion 112 and a fixed handle portion 114. Handle assembly 100 further includes an activation button 120 and a clamp trigger 130.

Body portion 112 of housing 110 is configured to support an ultrasonic transducer and generator assembly ("TAG") 300 including a generator assembly 310 and an ultrasonic transducer assembly 320. TAG 300 may be permanently engaged with body portion 112 of housing 110 or removable therefrom. Generator assembly 310 includes a housing 312 configured to house the internal electronics of generator assembly 310, and a cradle 314 configured to rotatably support ultrasonic transducer assembly 320. Alternatively, generator assembly 310 may be remotely disposed and coupled to ultrasonic surgical instrument 10 by way of a surgical cable. TAG 300 is described in greater detail below.

Fixed handle portion 114 of housing 110 defines a compartment 116 configured to receive a battery assembly 400 and a door 118 configured to enclose compartment 116. An electrical connection assembly 140 is disposed within housing 110 of handle assembly 100 and serves to electrically couple activation button 120, generator assembly 310 of TAG 300, and battery assembly 400 with one another when TAG 300 is supported on or in body portion 112 of housing 110 and battery assembly 400 is disposed within compartment 116 of fixed handle portion 114 of housing 110, thus enabling activation of ultrasonic surgical instrument 10 in response to depression of activation button 120. In embodiments where generator assembly 310 is remote from ultrasonic surgical instrument 10, battery assembly 400 and the configuration of fixed handle portion 114 for receiving battery assembly 400 need not be provided, as generator assembly 310 may be powered by a standard wall outlet or other power source.

Referring still to FIGS. 1 and 2, elongated assembly 200 of ultrasonic surgical instrument 10 includes an outer drive sleeve 210, an inner support sleeve 220 disposed within outer drive sleeve 210, a waveguide 230 extending through inner support sleeve 220, a drive assembly 250, a rotation knob 270, and an end effector 280 including a blade 282 and a jaw 284. A proximal portion of outer drive sleeve 210 is operably coupled to clamp trigger 130 of handle assembly 100 via drive assembly 250, while a distal portion of outer drive sleeve 210 is operably coupled to jaw 284. As such, clamp trigger 130 is selectively actuatable to thereby move outer drive sleeve 210 about inner support sleeve 220 to pivot jaw 284 relative to blade 282 of end effector 280 from a spaced-apart position to an approximated position for clamping tissue between jaw 284 and blade 282. Drive assembly 250 provides a force-limiting feature whereby the clamping pressure applied to tissue is limited to a particular clamping pressure or particular clamping pressure range. Rotation knob 270 is rotatable in either direction to rotate elongated assembly 200 in either direction relative to handle assembly 100.

Waveguide 230 extends through inner support sleeve 220. Waveguide 230 defines a body 232 and a blade 282 extending from the distal end of body 232. Blade 282 serves as the blade of end effector 280. Waveguide 230 further includes a proximal threaded male connector 236 configured for threaded engagement within threaded female receiver 325e of nose 325b of ultrasonic horn 324 of ultrasonic transducer assembly 320 such that ultrasonic vibrations produced by ultrasonic transducer assembly 320 are transmitted along waveguide 230 to blade 282 for treating tissue clamping between blade 282 and jaw 284 or positioned adjacent to blade 282.

Figure 3:
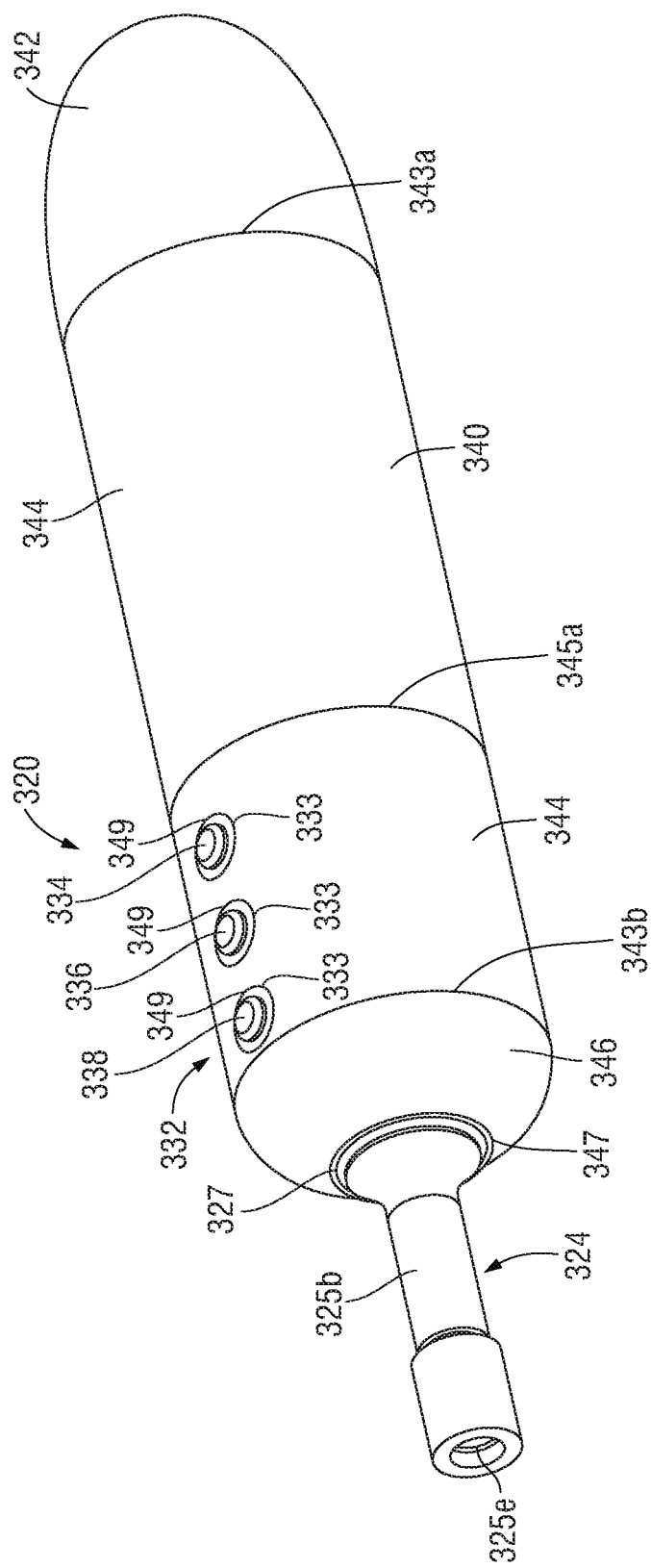
FIG. 3 is an enlarged, front, perspective view of the transducer assembly of the ultrasonic surgical instrument of FIG. 1.
Figure 4:
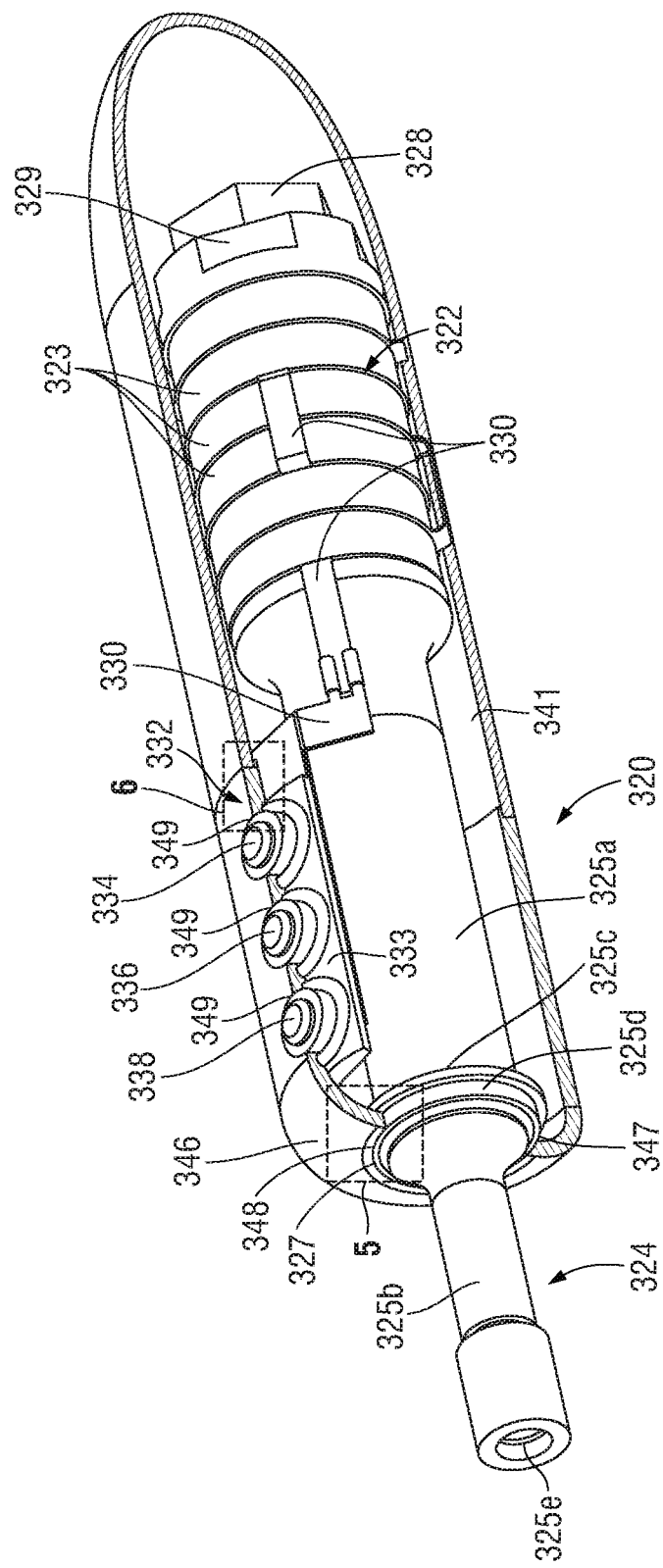
FIG. 4 is an enlarged, front, perspective view of the transducer assembly of the ultrasonic surgical instrument of FIG. 1 with a portion of the casing removed to illustrate the internal features and components thereof.

Referring to FIGS. 2-4, ultrasonic transducer assembly 320 includes a piezoelectric stack 322, an ultrasonic horn 324, a bolt 328 (FIG. 4), a proximal nut 329 (FIG. 4), first and second electrode assemblies 330, a contact assembly 332, and a casing 340. Bolt 328 secures piezoelectric stack 322 between ultrasonic horn 324 and a proximal nut 329. First and second electrode assemblies 330 are interdisposed between the piezoelectric elements 323 of piezoelectric stack 322 and connect to contact assembly 332. Contact assembly 332 enables communication of drive and/or data signals through casing 340, e.g., between piezoelectric stack 322 and generator assembly 310. Casing 340, together with ultrasonic horn 324, defines a hermetically sealed enclosure having an interior 341 that houses piezoelectric stack 322, a portion of ultrasonic horn 324, bolt 328, proximal nut 329, first and second electrode assemblies 330, and a portion of contact assembly 332.

Ultrasonic transducer assembly 320 further includes a rotation knob 350 (FIG. 1) mounted on or formed with casing 340 at the proximal end of casing 340. Rotation knob 350 is accessible from the exterior of handle assembly 100 and is configured for manual rotation to rotate ultrasonic transducer assembly 320 relative to generator assembly 310 and housing 110.

Continuing with reference to FIGS. 1 and 2, generator assembly 310 includes a plurality of ring contacts 364, 366, 368 surrounding ultrasonic transducer assembly 320 and disposed in slidable contact with corresponding slip contacts 334, 336, 338, respectively, of contact assembly 332 of ultrasonic transducer assembly 320. Thus, ring contacts 364, 366, 368 and respective slip contacts 334, 336, 338 define slip ring contact assemblies that enable drive and/or data signals to be communicated between generator assembly 310 and piezoelectric stack 322 of ultrasonic transducer assembly 320 regardless of the rotational orientation of ultrasonic transducer assembly 320 relative to generator assembly 310. More specifically, with respect to drive signal communication, the first of the electrode assemblies 330 includes at least one positive electrode disposed between the piezoelectric elements 323 of piezoelectric stack 322 and an electrode connector connecting the at least one positive electrode with slip contact 334 which, in turn, is disposed in contact with ring contact 364. The second of the electrode assemblies 330 includes at least one negative electrode disposed between the piezoelectric elements 323 of piezoelectric stack 322 and an electrode connector connecting the at least one negative electrode with slip contact 336 which, in turn, is disposed in contact with ring contact 366. As such, a drive signal voltage may be applied from generator assembly 310 across the piezoelectric elements 323 of the piezoelectric stack 322 via the positive and negative electrodes. The piezoelectric stack 322, in turn, converts the applied voltage into mechanical energy, in the form of ultrasonic vibrations, that is transmitted to ultrasonic horn 324. In other embodiments, the second of the electrode assemblies 330 is omitted and casing 340 is utilized as the negative electrode for piezoelectric stack 322.

With respect to data signal communication, contact assembly 332 may include a data chip (not explicitly shown) (or electrical connectors, with the data chip disposed within generator assembly 310) disposed in communication with ultrasonic horn 324 (and/or other portions of ultrasonic transducer assembly 320). The data chip, more specifically, may be a microprocessor chip or other suitable chip with sensory circuitry to detect various conditions, parameters, properties, etc. of piezoelectric stack 322, ultrasonic horn 324, and/or other portions of ultrasonic transducer assembly 320. The data chip may be configured to sense, for example, a frequency, amplitude, impedance, and/or temperature of ultrasonic horn 324 (or other portion of ultrasonic transducer assembly 320); the number of times ultrasonic transducer assembly 320 has been activated, the duration of activation ultrasonic transducer assembly 320, etc. The data chip may additionally or alternatively include a memory storing information relating to ultrasonic transducer assembly 320 such as, for example, model, serial number, manufacture date, calibration and/or testing information, manufacturer setting information, etc. In embodiments where the data chip includes sensor circuitry, the memory may also store the sensed data.

The data chip (or electrical connectors) within ultrasonic transducer assembly 320 are coupled to slip contact 338 of contact assembly 332 which, in turn, is disposed in contact with ring contact 368 to enable communication of data signals between ultrasonic transducer assembly 320 and ultrasonic generator assembly 310.

Ultrasonic horn 324 includes a body 325a disposed within casing 340 of ultrasonic transducer assembly 320 and a nose 325b extending distally from body 325a externally of casing 340 of ultrasonic transducer assembly 320. A proximal collar 325c is disposed between body 325a and nose 325b and an annular, outwardly-facing contact surface 325d is disposed distally adjacent proximal collar 325c to facilitate formation of a hermetic seal between casing 340 and ultrasonic horn 324, as detailed below. Annular, outwardly-facing contact surface 325d may be disposed at or near a nodal point along ultrasonic horn 324. Nose 325b of ultrasonic horn 324 defines a distal threaded female receiver 325e configured to enable releasable threaded engagement of waveguide 230 with ultrasonic horn 324. Ultrasonic horn 324 may be formed from a metal, e.g., titanium, aluminum, stainless steel, an amorphous metal, etc., or other suitable material(s).

Referring to FIGS. 3-6, casing 340 of ultrasonic transducer assembly 320, as noted above, defines a hermetically sealed enclosure having an interior 341 that houses piezoelectric stack 322, a portion of ultrasonic horn 324, bolt 328, proximal nut 329, first and second electrode assemblies 330, and a portion of contact assembly 332. Casing 340 may be formed from a metal, e.g., titanium, aluminum, stainless steel, an amorphous metal, etc., or other suitable material(s). Casing 340 may be formed from a plurality of casing components including, for example, a proximal cap portion 342, one or more intermediate tube portions 344, and a distal cap portion 346. Proximal cap portion 342 defines a closed proximal end and an open distal end, the intermediate tube portion(s) 344 defines open proximal and distal ends, and distal cap portion 346 defines an open proximal end and a reduced-diameter opening 347 at the distal end thereof. Distal cap portion 346 further defines an annular, inwardly-facing contact surface 348 surrounding the reduced-diameter opening 347. Casing 340 further includes one or more windows 349 defined therethrough for sealing receipt of contact assembly 332 therein, as detailed below.

The distal end of proximal cap portion 342 and the proximal end of the proximal-most intermediate tube portion 344 abut one another to define a joint 343a and are welded to one another annularly about joint 343a to secure and hermetically seal the distal end of proximal cap portion 342 and the proximal end of the proximal-most intermediate tube portion 344 with one another. One of the distal end of proximal cap portion 342 or the proximal end of the proximal-most intermediate tube portion 344 includes a flange (not explicitly shown, see flange 345b (FIG. 6)) overlapping, on the interior side thereof, joint 343a. By overlapping joint 343a, the flange protects the interior 341 of casing 340 (and any components disposed therein) as joint 343a is welded to secure and hermetically seal the distal end of proximal cap portion 342 and the proximal end of the proximal-most intermediate tube portion 344 with one another. As an alternative to welding, other suitable methods of securing and hermetically sealing the distal end of proximal cap portion 342 and the proximal end of the proximal-most intermediate tube portion 344 are also contemplated such as, for example, press-fitting, using O-rings, adhesion, etc.

The distal end of the distal-most intermediate tube portion 344 and the proximal end of distal cap portion 346 abut one another to define a joint 343b and are welded to one another annularly about joint 343b to secure and hermetically seal the distal end of the distal-most intermediate tube portion 344 and the proximal end of distal cap portion 346 with one another. One of the distal end of the distal-most intermediate tube portion 344 or the proximal end of distal cap portion 346 includes a flange (not explicitly shown, see flange 345b (FIG. 6)) overlapping, on the interior side thereof, joint 343b to protect the interior 341 of casing 340 as joint 343b is welded to secure and hermetically seal the distal end of the distal-most intermediate tube portion 344 and the proximal end of distal cap portion 346 with one another.

Figure 6:
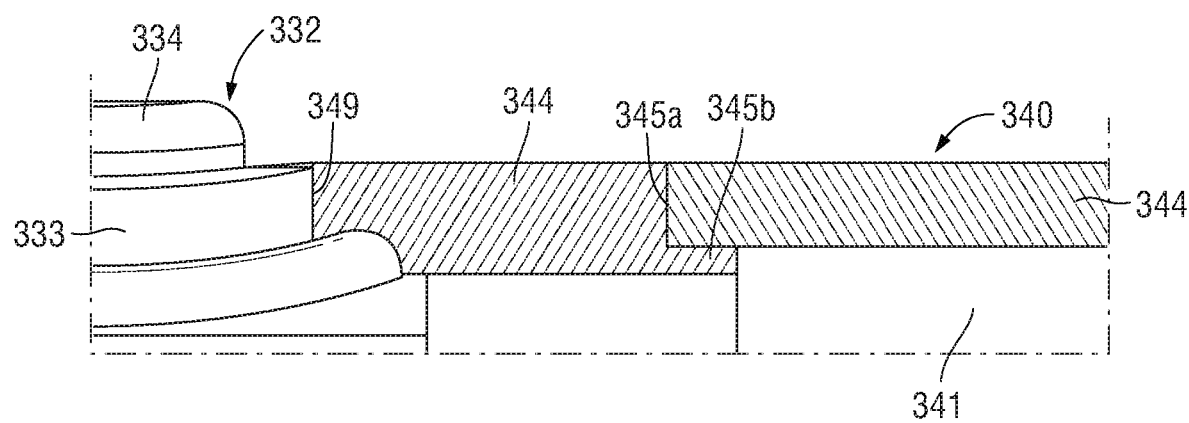
FIG. 6 is an enlarged, side view of the area of detail indicated as "6" in FIG. 4.

Turning to FIG. 6, in embodiments where multiple intermediate tube portions 344 are provide, the abutting ends of adjacent intermediate tube portions 344 may be welded to one another similarly as detailed above, e.g., with a flange 345b overlapping the weld joint 345a on the interior side thereof. As an alternative to including proximal, intermediate, and distal portions 342, 344, 346, respectively, welded to one another about annular joints, casing 340 may include, for example, left and right half portions welded to one another along a longitudinal joint, or may include any suitable combination of components welded to one another via annular and/or longitudinal joints (and including annular and/or longitudinal internal flanges). In other embodiments, casing 340 is formed as a single, monolithic piece of material.

Figure 5:
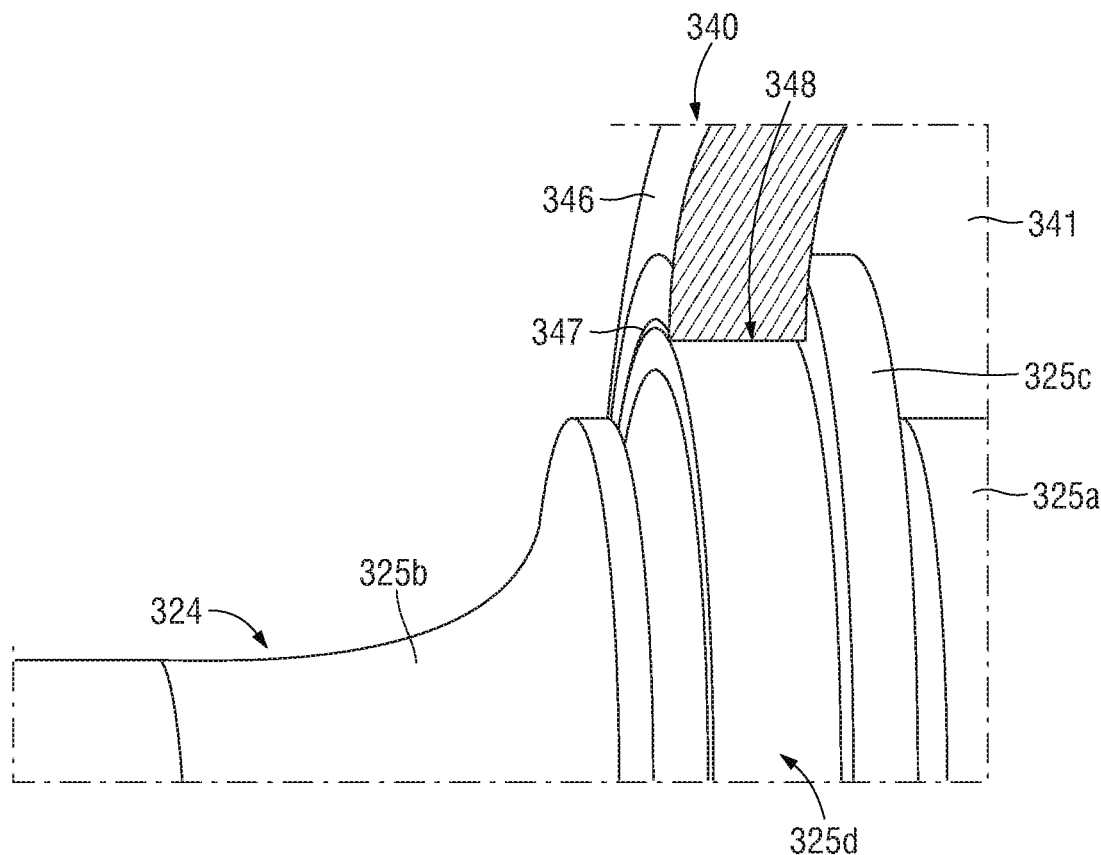
FIG. 5 is an enlarged, perspective view of the area of detail indicated as "5" in FIG. 4.

With particular reference back to FIG. 5, in order to fully enclose and hermetically seal interior 341 of casing 340, thus hermetically sealing piezoelectric stack 322, a portion of ultrasonic horn 324, bolt 328, proximal nut 329, first and second electrode assemblies 330, and a portion of contact assembly 332 within casing 340, distal cap portion 346 of casing 340 is positioned such that ultrasonic horn 324 extends through reduced-diameter opening 347. More specifically, casing 340 and ultrasonic horn 324 are positioned such that ultrasonic horn 324 extends through reduced-diameter opening 347 with proximal collar 325c abutting the interior surface of casing 340 adjacent reduced-diameter opening 347 and such that outwardly-facing contact surface 325d and inwardly-facing contact surface 348 abut one another to define a joint 327. Distal cap portion 346 of casing 340 and ultrasonic horn 324 are welded to one another annularly about joint 327 to secure and hermetically seal the distal end of distal cap portion 346 and ultrasonic horn 324 with one another. Proximal collar 325c overlaps joint 327, on the interior side thereof, to thereby protect the interior 341 of casing 340 (and any components disposed therein) as joint 327 is welded to secure and hermetically seal distal cap portion 346 of casing 340 and ultrasonic horn 324 with one another. As noted above, annular, outwardly-facing contact surface 325d of ultrasonic horn 324 may be disposed at a nodal point along ultrasonic horn 324 and, thus, joint 327 (where casing 340 is attached to ultrasonic horn 324) is likewise disposed at a nodal point along ultrasonic horn 324 such that casing 340 remains ultrasonically inert.

Referring to FIGS. 2 and 4, contact assembly 332, as noted above, includes slip contacts 334, 336, 338 extending from interior 341 of casing 340 to the exterior thereof. More specifically, contacts 334, 336, 338 protrude radially outwardly beyond the exterior surface of casing 340 to enable slidable contact with corresponding ring contacts 364, 366, 368, respectively, of generator assembly 310 without casing 340 contacting ring contacts 364, 366, 368. Further, as casing 340 is formed from an electrically-conductive material, e.g., a metal, contact assembly 332 further includes an electrically-insulative frame 333 sealingly retaining contacts 334, 336, 338 therein in electrical isolation from one another and casing 340. Frame 333 may be formed from a polymer or other suitable electrically-insulative material and may be overmolded about contacts 334, 336, 338 to secure and form a hermetic seal thereabout, hermetically sealed and secured about contacts 334, 336, 338 using an epoxy or other seal, or may be hermetically sealed and secured about contacts 334, 336, 338 in any other suitable manner. Further, frame 333 may be overmolded within window(s) 349 of casing 340 to secure contact assembly 332 therein and form a hermetic seal therebetween (via the same overmold as that securing and sealing contacts 334, 336, 338 or an additional overmold), may be secured and hermetically sealed within window(s) 349 using an epoxy or other seal, or may be secured and hermetically sealed within window(s) 349 in any other suitable manner.

The above-detailed hermetic sealing of casing 340 to ultrasonic horn 324 (as well as hermetically sealing contact assembly 332 within window(s) 349 of casing 340) ensures that transducer assembly 320 is capable of withstanding multiple rounds of sterilization, e.g., autoclave sterilization.

While several embodiments of the disclosure have been detailed above and are shown in the drawings, it is not intended that the disclosure be limited thereto, as it is intended that the disclosure be as broad in scope as the art will allow and that the specification be read likewise. Therefore, the above description and accompanying drawings should not be construed as limiting, but merely as exemplifications of particular embodiments. Those skilled in the art will envision other modifications within the scope and spirit of the claims appended hereto.

What is claimed is:

1. An ultrasonic transducer assembly of an ultrasonic surgical instrument, comprising:
   a piezoelectric stack;
   an ultrasonic horn secured to and extending distally from the piezoelectric stack, the ultrasonic horn including a body and a nose extending distally from the body; and
   a casing disposed about the piezoelectric stack and the body of the ultrasonic horn, the casing defining a distal opening through which the nose of the ultrasonic horn extends, the casing hermetically sealed to the ultrasonic horn by directly attaching the casing to the ultrasonic horn about the distal opening to define a hermetically sealed interior enclosing the piezoelectric stack and the body of the ultrasonic horn therein.

2. The ultrasonic transducer assembly according to claim 1, wherein the casing is welded to the ultrasonic horn along a weld joint surrounding the distal opening.

3. The ultrasonic transducer assembly according to claim 2, wherein the ultrasonic horn includes a flange disposed between the body and the nose, the flange disposed within the hermetically sealed interior adjacent the distal opening and overlapping the weld joint.

4. The ultrasonic transducer assembly according to claim 1, wherein the casing is hermetically sealed to the ultrasonic horn at a nodal point along the ultrasonic horn.

5. The ultrasonic transducer assembly according to claim 1, wherein the casing includes at least two casing components hermetically sealed to one another.

6. The ultrasonic transducer assembly according to claim 5, wherein the at least two casing components are welded to one another along at least one additional weld joint.

7. The ultrasonic transducer assembly according to claim 6, wherein one of the at least two casing components includes a flange disposed within the hermetically sealed interior and overlapping the at least one additional weld joint.

8. The ultrasonic transducer assembly according to claim 1, further comprising a contact assembly hermetically sealed within at least one window defined through the casing, the contact assembly including a plurality of contacts extending from the hermetically sealed interior to an exterior of the casing.

9. The ultrasonic transducer assembly according to claim 8, wherein the contact assembly further includes a frame electrically isolating the plurality of contacts from the casing.

10. The ultrasonic transducer assembly according to claim 8, wherein at least one of the contacts is configured to communicate a drive signal into the hermetically sealed interior and wherein at least another one of the contacts is configured to communicate a data signal from the hermetically sealed interior.

11. An ultrasonic surgical instrument, comprising:
   a handle assembly, including:
      a housing;
      an ultrasonic transducer assembly supported by the housing, including:
         a piezoelectric stack;
         an ultrasonic horn secured to and extending distally from the piezoelectric stack, the ultrasonic horn including a body and a nose extending distally from the body; and a casing disposed about the piezoelectric stack and the body of the ultrasonic horn, the casing defining a distal opening through which the nose of the ultrasonic horn extends, the casing hermetically sealed to the ultrasonic horn by directly attaching the casing to the ultrasonic horn about the distal opening to define a hermetically sealed interior enclosing the piezoelectric stack and the body of the ultrasonic horn therein; and an elongated assembly extending distally from the handle assembly, the elongated assembly including a waveguide configured to engage the nose of the ultrasonic horn, the waveguide defining a blade at a distal end thereof, wherein ultrasonic energy produced by the piezoelectric stack is transmitted along the ultrasonic horn and the waveguide to the blade for treating tissue adjacent the blade.

12. The ultrasonic surgical instrument according to claim 11, wherein the casing is welded to the ultrasonic horn along a weld joint surrounding the distal opening.

13. The ultrasonic surgical instrument according to claim 12, wherein the ultrasonic horn includes a flange disposed between the body and the nose, the flange disposed within the hermetically sealed interior adjacent the distal opening and overlapping the weld joint.

14. The ultrasonic surgical instrument according to claim 11, wherein the casing is hermetically sealed to the ultrasonic horn at a nodal point along the ultrasonic horn.

15. The ultrasonic surgical instrument according to claim 11, wherein the casing includes at least two casing components hermetically sealed to one another along at least one additional weld joint.

16. The ultrasonic surgical instrument according to claim 15, wherein one of the at least two casing components includes a flange disposed within the hermetically sealed interior and overlapping the at least one additional weld joint.

17. The ultrasonic surgical instrument according to claim 11, further comprising a contact assembly hermetically sealed within at least one window defined through the casing, the contact assembly including a plurality of slip contacts extending from the hermetically sealed interior to an exterior of the casing.

18. The ultrasonic surgical instrument according to claim 17, further comprising a plurality of ring contacts disposed within the handle assembly, each ring contact configured to slidable couple to a corresponding slip contact of the plurality of slip contacts.

19. The ultrasonic surgical instrument according to claim 18, wherein at least one pair of a ring contact and a corresponding slip contact is configured to communicate a drive signal into the hermetically sealed interior.

20. The ultrasonic surgical instrument according to claim 18, wherein at least one pair of a ring contact and a corresponding slip contact is configured to communicate a data signal from the hermetically sealed interior.

* * * * *